US012496217B2

(12) United States Patent
Kim et al.

(10) Patent No.: US 12,496,217 B2
(45) Date of Patent: Dec. 16, 2025

(54) SYSTEM FOR CIRCULATING HYPERTHERMIC PRESSURIZED GAS IN PERITONEAL CAVITY, AND INTRAPERITONEAL GAS PROVIDING SYSTEM INCLUDING TWO-FLUID NOZZLE

(71) Applicants: Seoul National University Hospital, Seoul (KR); Seoul National University R&DB Foundation, Seoul (KR)

(72) Inventors: Hyung-Ho Kim, Seongnam-Si (KR); Koo Tae Kang, Seoul (KR)

(73) Assignee: SILVER LINING MEDICAL INC., Hanam-si (KR)

( * ) Notice: Subject to any disclaimer, the term of this patent is extended or adjusted under 35 U.S.C. 154(b) by 1005 days.

(21) Appl. No.: 17/626,972

(22) PCT Filed: Jul. 15, 2020

(86) PCT No.: PCT/KR2020/009328
§ 371 (c)(1),
(2) Date: Jul. 12, 2022

(87) PCT Pub. No.: WO2021/010750
PCT Pub. Date: Jan. 21, 2021

(65) Prior Publication Data

US 2022/0339026 A1 Oct. 27, 2022

(30) Foreign Application Priority Data

Jul. 15, 2019 (KR) ........................ 10-2019-0085381
Jul. 15, 2019 (KR) ........................ 10-2019-0085382

(51) Int. Cl.
*A61F 7/12* (2006.01)
*A61M 11/00* (2006.01)
*A61F 7/00* (2006.01)

(52) U.S. Cl.
CPC ............. *A61F 7/12* (2013.01); *A61M 11/007* (2014.02); *A61F 2007/006* (2013.01);
(Continued)

(58) Field of Classification Search
CPC ........ A61F 2007/0059; A61F 2007/006; A61F 2007/0069; A61F 2007/0096;
(Continued)

(56) References Cited

U.S. PATENT DOCUMENTS 9,387,295 B1 7/2016 Mastri et al.
2005/0234398 A1 10/2005 Wood, Jr.
(Continued)

FOREIGN PATENT DOCUMENTS

CN 201744066 U 2/2011
CN 102341049 A 2/2012
(Continued)

OTHER PUBLICATIONS

Jung, Do Hyun et. al.; "Feasibility of hyperthermic pressurized intraperitoneal aerosol chemotherapy in a porcine model"; Surgical Endoscopy; vol. 30 No. 10; 2015; pp. 4258-4264.
(Continued)

*Primary Examiner* — Tigist S Demie
(74) *Attorney, Agent, or Firm* — Jackson Walker LLP

(57) ABSTRACT

Disclosed are: a system comprising a gas circulation device capable of circulating hyperthermic gas in the peritoneal cavity and a temperature control device; and a system comprising a drug spray device for effectively spraying a drug in the peritoneal cavity together with gas. The systems of the present invention are used as systems for hyperthermic intraperitoneal chemotherapy and can maximize the anticancer therapy effect by more effectively delivering a small amount of an anticancer drug to cancer cells while
(Continued)

maintaining the temperature of gas in the peritoneal cavity at a predetermined temperature.

18 Claims, 11 Drawing Sheets

(52) U.S. Cl.
CPC ................ *A61F 2007/0096* (2013.01); *A61M 2202/0225* (2013.01); *A61M 2210/1017* (2013.01)

(58) Field of Classification Search
CPC ... A61F 2007/126; A61F 7/12; A61M 11/007; A61M 11/02; A61M 13/006; A61M 16/1095; A61M 2202/0021; A61M 2202/0225; A61M 2205/3368; A61M 2205/3653; A61M 2210/1017; A61M 2230/005; A61M 2230/50
See application file for complete search history.

(56) References Cited

U.S. PATENT DOCUMENTS

| | | | | |
|---|---|---|---|---|
| 2010/0268153 | A1 | 10/2010 | Mantell | |
| 2011/0087160 | A1 | 4/2011 | Temple | |
| 2015/0250957 | A1 | 9/2015 | Albalat | |
| 2015/0253205 | A1 | 9/2015 | Hauser et al. | |
| 2019/0192792 | A1* | 6/2019 | Albalat | A61M 31/00 |

FOREIGN PATENT DOCUMENTS

| | | | |
|---|---|---|---|
| CN | 204485048 | U | 7/2015 |
| DE | 102017006185 | A1 * | 1/2019 |
| EP | 1402909 | A1 | 3/2004 |
| JP | 2004-216320 | A | 8/2004 |
| JP | 2005-176908 | A | 7/2005 |
| JP | 2007-507317 | A | 3/2007 |
| JP | 6022534 | B2 | 11/2016 |
| JP | 2016-209344 | A | 12/2016 |
| JP | 2018-164857 | A | 10/2018 |
| KR | 10-1866455 | B1 | 6/2018 |
| KR | 10-2019-0069608 | A | 6/2019 |
| WO | 2004043534 | A1 | 5/2004 |

OTHER PUBLICATIONS

"International Search Report"; prepared for application No. PCT/KR2020/009328; Oct. 26, 2020; 6 pages.

* cited by examiner

SYSTEM FOR CIRCULATING HYPERTHERMIC PRESSURIZED GAS IN PERITONEAL CAVITY, AND INTRAPERITONEAL GAS PROVIDING SYSTEM INCLUDING TWO-FLUID NOZZLE

TECHNICAL FIELD

The present invention relates to a system for circulating hyperthermic pressurized gas in a peritoneal cavity, and more specifically, to a system including a gas circulation device capable of circulating hyperthermic gas in the peritoneal cavity, a temperature control device, and a drug spray device that effectively sprays a drug together with gas in the peritoneal cavity. In addition, the present invention relates to an intraperitoneal gas providing system including a two-fluid nozzle through which a drug such as an anticancer drug is effectively sprayed in a peritoneal cavity to treat a patient's cancer or the like, particularly, to a system for circulating hyperthermic pressurized gas in the peritoneal cavity. The systems of the present invention are particularly effective as systems for hyperthermic intraperitoneal chemotherapy.

BACKGROUND ART

Recently, the intraperitoneal chemotherapy (IPC) is carried out as a method for resolving a low efficiency of a drug which is orally or intravascularly administered to cancer cells that metastasize in a peritoneal cavity.

A pressurized intraperitoneal aerosol chemotherapy (PIPAC) may have a chemotherapy effect by directly spraying a nebulized drug to cancer cells only with about 10% of an anticancer drug dosage used in the hyperthermic intraperitoneal chemotherapy (HIPEC); However, there is a problem that a temperature in the peritoneal cavity is difficult to maintain at a temperature of about 42° C., at which cancer cells die, due to temperature homeostasis (36° C.) of a human body.

Further, the HIPEC allows the temperature to be maintained at about 42° C. but has a problem of easily leading to chemotherapy side effects due to a large amount of anticancer drug and an extensive surgical procedure.

In addition, the existing methods have a problem that an anticancer drug is difficult to be evenly sprayed in a peritoneal cavity and a spraying direction is difficult to adjust.

PRIOR ART LITERATURE

Patent Literature

1. Korean Patent Registration No. 1866455

DISCLOSURE

Technical Problem

In order to solve the problems described above, in one aspect, an object of the present invention is to provide a system for circulating hyperthermic pressurized gas in a peritoneal cavity so as to increase a therapy effect by including a gas circulation device and a temperature control device which can circulate gas in the peritoneal cavity at a set temperature and pressure.

In another aspect, an object of the present invention is to provide a system including a drug-and-gas spray device that can effectively spray a drug together with gas in a peritoneal cavity and can more effectively deliver the drug such as an anticancer drug to a lesion in the peritoneal cavity.

Solution to Problem

In one aspect, to achieve the object, a system (apparatus) for circulating hyperthermic pressurized gas in a peritoneal cavity according to exemplary embodiments of the present invention includes a gas circulation device that includes a gas hose which is connected to a peritoneal cavity of a subject and a pump which is connected to the gas hose and that circulates gas discharged from the peritoneal cavity back to the peritoneal cavity; and a temperature control device that controls a gas temperature of the gas circulation device such that gas in the peritoneal cavity has a set temperature.

The gas circulation device may include: an intraperitoneal gas injector through which gas is injected into the peritoneal cavity; and a circulation unit which discharges gas to outside from the peritoneal cavity, circulates the gas at the outside of the peritoneal cavity, and injects the gas back into the peritoneal cavity. The temperature control device may include: a temperature sensor which measures at least one of a gas temperature in the peritoneal cavity and a gas temperature of the gas circulation device at the outside of the peritoneal cavity; a heater that provides heat to at least a part of the gas hose of the gas circulation device; and a temperature controller that is connected to the heater and the temperature sensor. The temperature controller may control temperature of the heater such that a gas temperature in the peritoneal cavity reaches a set temperature based on a measured value of the temperature sensor.

Further, the intraperitoneal gas injector may include a drug-and-gas spray device that sprays a drug together with gas during gas injection into the peritoneal cavity of the subject.

Meanwhile, in order to achieve the above-described object, in the other aspect, an intraperitoneal gas providing system of exemplary embodiments of the present invention includes a drug-and-gas spray device. The drug-and-gas spray device includes: a drug syringe which supplies a drug; a drug-and-gas dispenser which is supplied with gas, is supplied with a drug from the drug syringe, and is cannulated into a peritoneal cavity to dispense a drug and gas into the peritoneal cavity of the subject; and a two-fluid nozzle which is disposed at an end of the drug-and-gas dispenser and through which the drug and gas are together sprayed into the peritoneal cavity.

In addition, the system may be a system for circulating hyperthermic pressurized gas in the peritoneal cavity, particularly, a system for hyperthermic intraperitoneal chemotherapy.

The system may include: a gas circulation device that includes a gas hose which is connected to the peritoneal cavity of a subject and a pump which is connected to the gas hose and circulates gas and that circulates gas discharged from the peritoneal cavity back to the peritoneal cavity; and a temperature control device that controls a gas temperature of the gas circulation device such that gas in the peritoneal cavity has a set temperature. Here, the above-described drug-and-gas spray device may be included as for the intraperitoneal gas injector of the gas circulation device.

Advantageous Effects of the Invention

According to the systems of exemplary embodiments of the present invention, temperature in a peritoneal cavity may be effectively maintained by supplying gas such as carbon dioxide, which dilates the peritoneal cavity of a subject, and heating the gas while circulating the gas in the peritoneal cavity with a circulation pump of a circulation unit.

Further, according to the system of the exemplary embodiments of the present invention, gas such as carbon dioxide for dilating the peritoneal cavity of the subject is sprayed together with a nebulized drug such as an anticancer drug into the dilated peritoneal cavity through a two-fluid nozzle, and thereby the anticancer drug insufflated at a high pressure can be nebulized to a high extent to be evenly sprayed in the peritoneal cavity, and also a spray direction is allowed to be very easy to adjust. As described above, since the nebulized anticancer drug can be evenly dispersed in the dilated peritoneal cavity so as to effectively work on a peritoneum to which the cancer cells metastasize, a cancer therapy effect can be maximized.

Therefore, when the systems of the exemplary embodiments of the present invention are used as systems for hyperthermic intraperitoneal chemotherapy, it can maximize the anticancer therapy effect by more effectively delivering a small amount of an anticancer drug to cancer cells while maintaining the gas temperature of the peritoneal cavity at a set temperature.

[Description of Reference Numbers]

Figure 1:
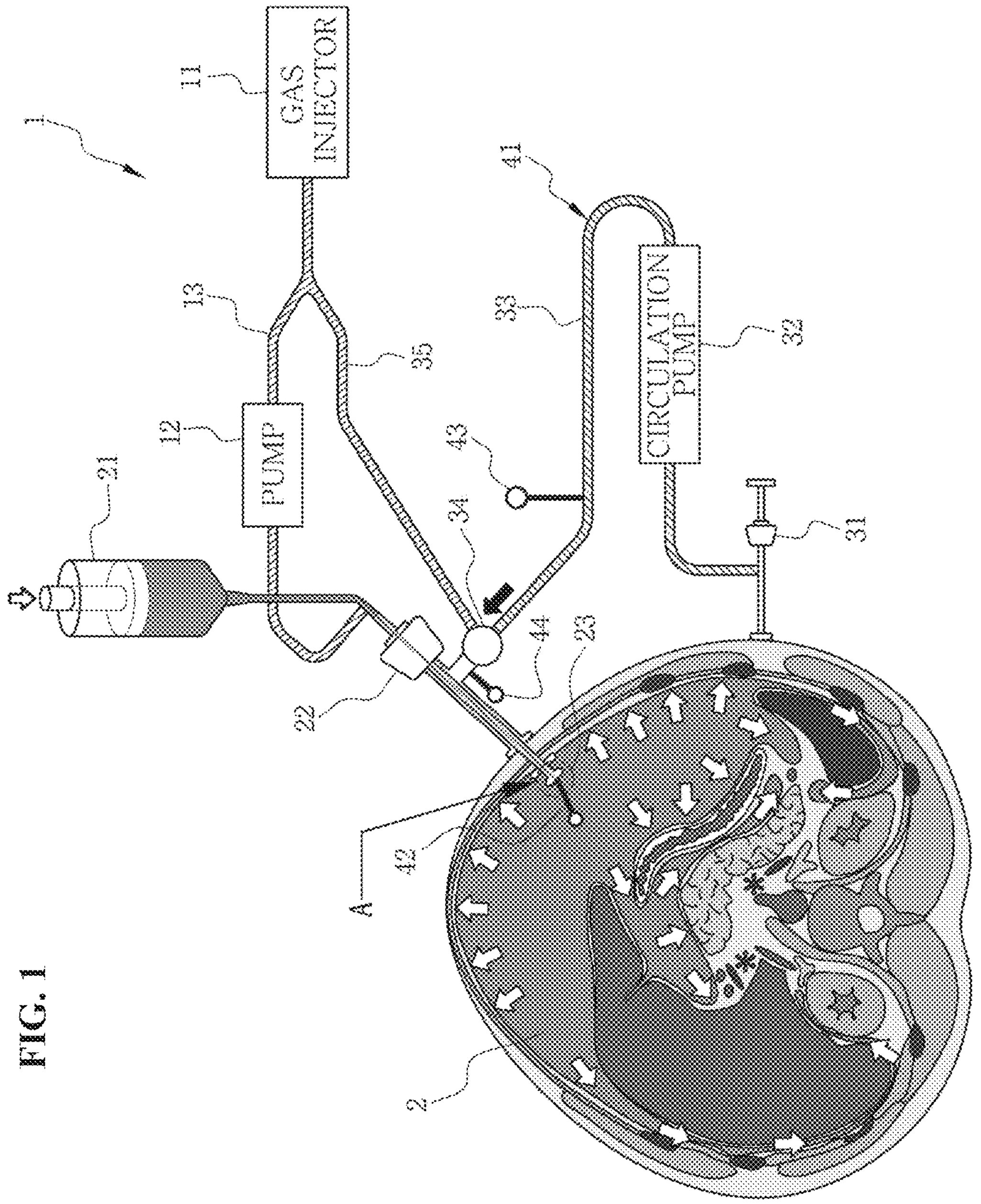
FIG. 1 is a schematic diagram illustrating a configuration of a system apparatus according to a first example of the present invention.

| | |
|---|---|
| 1: System | 2: Inside of Peritoneal Cavity |
| 10: Gas Supply Unit | 11: Gas Injector |
| 12: Pump | 13: First Hose |
| 20: Drug Spray Device | 21: Drug Syringe |
| 22: Drug Dispenser | 23(23'): Nozzle (Two-Fluid Nozzle) |
| 30: Circulation Unit | 31: First Trocar |
| 32: Circulation Pump | 33: Circulation Hose |
| 34: Circulation Valve | 35: Second Hose |
| 37: Second Trocar | 40: Temperature Controller |
| 41: Hot Wire Coil | 42: First Temperature Sensor |
| 43: Second Temperature Sensor | 44: Third Temperature Sensor |
| 231: Drug Line | 232: Gas Line |
| 233: Mixing Chamber | 234: Outlet |

MODE FOR INVENTION

One Aspect

In one aspect, detailed description of exemplary embodiments of the present invention are as follows.

A system (apparatus) according to the exemplary embodiments of the one aspect of the present invention is a system (apparatus) for circulating hyperthermic pressurized gas in a peritoneal cavity and mainly includes a gas circulation device and a temperature control device.

The gas circulation device includes a gas hose which is connected to the peritoneal cavity of a subject and one or more pumps which are connected to the gas hose and circulate and pressurize gas, and the gas circulation device circulates gas discharged from the peritoneal cavity back to the peritoneal cavity.

In an embodiment, the gas circulation device may include an intraperitoneal gas injecting unit through which pressurized gas is injected into the peritoneal cavity and a circulation unit which discharges gas to the outside from the peritoneal cavity, circulates the gas at the outside of the peritoneal cavity, and injects the gas back into the peritoneal cavity.

In an embodiment, the intraperitoneal gas injecting unit may include one or more drug-and-gas spray devices that spray a drug together with gas during gas injection into the peritoneal cavity of the subject. In addition, the intraperitoneal gas injecting unit may further include one or more cannulation devices (gas supply trocars) which are cannulated into the peritoneal cavity to supply gas, separately from the drug-and-gas spray device.

In an embodiment, the drug-and-gas spray device may include a drug syringe which supplies a drug, a drug-and-gas dispenser which is connected to the gas hose to be supplied with pressurized gas, is supplied with a drug from the drug syringe, and is cannulated into the peritoneal cavity to dispense a drug and gas into the peritoneal cavity of the subject. A nozzle through which the drug and gas are sprayed into the peritoneal cavity can be disposed at an end of the drug-and-gas dispenser.

In an embodiment, the drug-and-gas dispenser may be configured to include, for example, a head, a body part extending from the head, and a peritoneal cavity cannulation unit under the body part. The gas hose may be connected to at least one of the head and the body part to supply gas. In addition, as described below, a temperature sensor may be mounted on one side of the body part.

In an embodiment, it is desirable that the nozzle be particularly a two-fluid nozzle, as described below. Spraying from the nozzle is performed at a pressure lower than a pressure in the peritoneal cavity, for example at 6 to 14 mmHg or 6 to 15 mmHg.

In an embodiment, the gas circulation unit may include a circulation hose as a gas hose of the circulation unit and one or more circulation pumps which are connected to the circulation hose and increase pressure of circulating gas.

The circulating gas of the gas circulation unit may be discharged from a gas discharge unit, be circulated in the circulation unit by the pump, be heated and/or pressurized through the temperature control device as described below, and then be provided back into the intraperitoneal gas injecting unit.

Herein, the circulating gas of the gas circulation unit may be supplied to the drug-and-gas dispenser, or to a gas inflow trocar which is cannulated into the peritoneal cavity, or to both the drug-and-gas dispenser and the gas inflow trocar.

In an embodiment, the gas circulation device may further include a gas supply unit for supplying gas. The gas supply unit may be configured to be connected to at least one of the intraperitoneal gas injecting unit and the gas circulation unit of the gas circulation device.

For example, in an embodiment, the gas supply unit may be connected to supply gas to the drug-and-gas spray device of the intraperitoneal gas injecting unit. The gas supply unit may include a gas injector that generates gas and a gas hose (first hose) through which gas from the gas injector flows and which is connected to the drug-and-gas spray device. In addition, the gas supply unit may further include a pump that increases pressure of gas which flows through the gas hose.

In an embodiment, the gas hose of the gas supply unit may further include one or more branched gas hoses (second hoses). As described above, the branched hose may be connected to the circulation unit.

In addition, in an embodiment, the gas supply unit which supplies gas may be directly connected to the circulation unit. The gas supply unit may include a gas injector that generates gas and a gas hose (third hose) (not illustrated) through which gas from the gas injector flows and which is connected to the circulation unit.

In an embodiment, the gas circulation unit may include one or more valves to which two or more gas hoses are connected.

For example, the circulation unit may include a valve (first valve) to which the circulation hose and the hose (second hose) branched from the gas hose (first hose) of the above-described gas supply unit are connected and which discharges gas to the drug-and-gas dispenser.

In addition, the circulation unit may include a valve (second valve) to which the third hose and the circulation hose are connected and which discharges gas to the circulation pump.

In addition, the circulation unit may further include a valve (third valve) into which gas flows from the circulation pump and which provides the gas to the drug-and-gas dispenser. One or more gas hoses from the third valve may be connected to the drug-and-gas dispenser. For example, two gas hoses from the third valve may be connected to different locations of the drug-and-gas dispenser, or one gas hose from the third valve may be connected to the drug-and-gas dispenser and the other gas hose may be connected to the second trocar.

Meanwhile, the temperature control device controls a gas temperature of the gas circulation device such that gas in the peritoneal cavity has a set temperature. For this, the temperature control device measures at least one of a gas temperature in the peritoneal cavity and a gas temperature of the gas circulation device at the outside of the peritoneal cavity, and the temperature control device may control the gas temperature in the peritoneal cavity based on the at least one of the gas temperatures.

Specifically, in an embodiment, the temperature control device may include one or more temperature sensors which measure at least one of a gas temperature in the peritoneal cavity and a gas temperature of the gas circulation device at the outside of the peritoneal cavity, a heater such as a hot wire coil that provides heat to at least a part of the gas hose of the gas circulation device, and a temperature controller that is connected to the heater and the temperature sensors.

The temperature controller may control temperature of the heater such that a gas temperature in the peritoneal cavity is maintained at a set temperature, for example from 38° C. to 42° C., based on a measured value of the temperature sensor.

A plurality of temperature sensors may be provided. That is, the system of the present invention may include at least a first temperature sensor which measures temperature of gas sprayed into the peritoneal cavity and may include one or more additional sensors which measure temperature of the gas hose of the gas circulation device. For example, the temperature control device may further include one or more of: a second temperature sensor which measures temperature of gas of the circulation hose of the circulation unit, and a third temperature sensor which measures temperature of gas that is supplied from the circulation unit to the drug-and-gas dispenser.

In an embodiment, gas supply from each gas hose may be adjusted based on measured values of one or more of the second temperature sensor and the third temperature sensor. That is, since temperatures of gases flowing through the gas hoses such as the circulation hose, the first hose, and the second hose may be different from each other, temperature of gas which is injected into the peritoneal cavity may be adjusted by adjusting a flow amount of gas of each gas hose based on temperature measurement value of one or more of the second temperature sensor and the third temperature sensor.

In an embodiment, the gas of the system may be carbon dioxide.

In an embodiment, the system for circulating hyperthermic pressurized gas in the peritoneal cavity may be particularly a system for hyperthermic intraperitoneal chemotherapy, and the drug may be an anticancer drug.

As described above, when the hyperthermic intraperitoneal chemotherapy is carried out by using the above-described system, the temperature and pressure of gas in the peritoneal cavity may be effectively maintained, the drug can be evenly sprayed into the peritoneal cavity, and thereby a chemotherapy effect can be maximized Other Aspect Meanwhile, detailed description of exemplary embodiments of the present invention in other aspect are as follows.

In other aspect, a system (apparatus) according to the exemplary embodiments of the present invention is an intraperitoneal gas providing system including a drug-and-gas spray device, particularly, a system for circulating hyperthermic pressurized gas in the peritoneal cavity, particularly, a system for hyperthermic intraperitoneal chemotherapy.

The system may include the gas circulation device including a drug-and-gas spray device and a temperature control device, which will be described below in detail respectively.

The gas circulation device includes a gas hose, which is connected to the peritoneal cavity of a subject, and one or more pumps which are connected to the gas hose and circulate and pressurize gas, and the gas circulation device circulates gas discharged from the peritoneal cavity back to the peritoneal cavity.

In an embodiment, the gas circulation device may include an intraperitoneal gas injecting unit through which pressurized gas is injected into the peritoneal cavity and a circulation unit which discharges gas to the outside from the peritoneal cavity, circulates the gas at the outside of the peritoneal cavity, and injects the gas back into the peritoneal cavity.

In an embodiment, the intraperitoneal gas injecting unit may include one or more of the above-described drug-and-gas spray devices that spray a drug together with gas during gas injection into the peritoneal cavity of the subject. In addition, the intraperitoneal gas injecting unit may further include one or more cannulation devices (gas supply trocars) which are cannulated into the peritoneal cavity to supply gas, separately from the drug-and-gas spray device.

In an embodiment, the drug-and-gas spray device may include a drug syringe which supplies a drug, a drug-and-gas dispenser which is connected to the gas hose to be supplied with pressurized gas, is supplied with a drug from the drug syringe, and is cannulated into the peritoneal cavity to dispense a drug and gas into the peritoneal cavity of the subject. A two-fluid nozzle through which the drug and gas are sprayed into the peritoneal cavity may be disposed at an end of the drug-and-gas dispenser.

In an embodiment, the drug-and-gas dispenser may be configured to include, for example, a head, a body part extending from the head, and a peritoneal cavity cannulation unit under the body part. The gas hose may be connected to one or more of the head and the body part to supply gas. In addition, as described below, a temperature sensor may be mounted on one side of the body part.

In an embodiment, the two-fluid nozzle has a structure in which a drug and gas are dispensed together. For example, the two-fluid nozzle may include one or more drug lines to which a drug is supplied and one or more gas lines which are gas supply passages, and may selectively include one or more mixing chambers in which gas and a drug are mixed. In addition, the two-fluid nozzle may include one or more of outlets which are fine holes positioned in the front of the nozzle.

In an embodiment, spray from the two-fluid nozzle is performed at a pressure lower than a pressure in the peritoneal cavity, for example at 6 to 14 mmHg or 6 to 15 mmHg Spray pressure may be adjusted by a size of each line, a size of the fine hole, presence and absence of the mixing chamber, etc.

As described above, when the two-fluid nozzle is used, a high-pressure drug and pressurized gas are together sprayed into the peritoneal cavity so as to obtain an excellent degree of nebulization. Further, in a case of a single-fluid nozzle which supplies only a drug, the drug is difficult to spray to a desired lesion in the peritoneal cavity, and a spray direction is difficult to control; In contrast, when the two-fluid nozzle is used, the spray direction is easier to adjust, and thus the two-fluid nozzle is very suitable for performing chemotherapy in the peritoneal cavity.

In an embodiment, the gas circulation unit may include a circulation hose as a gas hose of the circulation unit and one or more of circulation pumps which are connected to the circulation hose and increase pressure of circulating gas.

The circulating gas of the gas circulation unit may be discharged from a gas discharge unit, be circulated in the circulation unit by the pump, be heated and/or pressurized through the temperature control device as described below, and then be provided back into the intraperitoneal gas injecting unit.

Herein, the circulating gas of the gas circulation unit may be supplied to the drug-and-gas dispenser, to a gas inflow trocar which is cannulated into the peritoneal cavity, or to both the drug-and-gas dispenser and the gas inflow trocar.

In an embodiment, the gas circulation device may further include a gas supply unit for supplying gas. The gas supply unit may be configured to be connected to one or more of the intraperitoneal gas injecting unit and the gas circulation unit of the gas circulation device.

For example, in an embodiment, the gas supply unit may be connected to supply gas to the drug-and-gas spray device of the intraperitoneal gas injecting unit. The gas supply unit can include a gas injector that generates gas and a gas hose (first hose) through which gas from the gas injector flows and which is connected to the drug-and-gas spray device. In addition, the gas supply unit can further include a pump that increases pressure of gas which flows through the gas hose.

In an embodiment, the gas hose of the gas supply unit may further include one or more of branched gas hoses (second hoses). As described above, the branched hose may be connected to the circulation unit.

In addition, in an embodiment, the gas supply unit which supplies gas may be directly connected to the circulation unit. The gas supply unit may include a gas injector that generates gas and a gas hose (third hose) (not illustrated) through which gas from the gas injector flows and which is connected to the circulation unit.

In an embodiment, the gas circulation unit may include one or more valves to which two or more gas hoses are connected.

For example, the circulation unit nay include a valve (first valve) to which the circulation hose and the hose (second hose) branched from the gas hose (first hose) of the above-described gas supply unit are connected and which discharges gas to the drug-and-gas dispenser.

In addition, the circulation unit may include a valve (second valve) to which the third hose and the circulation hose are connected and which discharges gas to the circulation pump.

In addition, the circulation unit may further include a valve (third valve) into which gas flows from the circulation pump and which provides the gas to the drug-and-gas dispenser. One or more gas hoses from the third valve may be connected to the drug-and-gas dispenser. For example, two gas hoses from the third valve may be connected to different locations of the drug-and-gas dispenser, or one gas hose from the third valve may be connected to the drug-and-gas dispenser and the other gas hose may be connected to the second trocar.

Meanwhile, the temperature control device controls a gas temperature of the gas circulation device such that gas in the peritoneal cavity has a set temperature. For this, the temperature control device may measure one or more of a gas temperature in the peritoneal cavity and a gas temperature of the gas circulation device at the outside of the peritoneal cavity, and the temperature control device may control the gas temperature in the peritoneal cavity based on the at least one of the gas temperatures.

Specifically, in an embodiment, the temperature control device may include one or more of temperature sensors which measure one or more of a gas temperature in the peritoneal cavity and a gas temperature of the gas circulation device at the outside of the peritoneal cavity, a heater such as a hot wire coil that provides heat to at least a part of the gas hose of the gas circulation device, and a temperature controller that is connected to the heater and the temperature sensors.

The temperature controller may control temperature of the heater such that a gas temperature in the peritoneal cavity is maintained at a set temperature of 38° C. to 42° C., for example, based on a measured value of the temperature sensor.

A plurality of temperature sensors may be provided. That is, the system of the present invention may include at least a first temperature sensor which measures temperature of gas sprayed into the peritoneal cavity, and may include one or more additional sensors which measure temperature of the gas hose of the gas circulation device. For example, the temperature control device may further include one or more of a second temperature sensor which measures temperature of gas of the circulation hose of the circulation unit and a third temperature sensor which measures temperature of gas that is supplied from the circulation unit to the drug-and-gas dispenser.

In an embodiment, gas supply from each gas hose may be adjusted based on measured values of one or more of the second temperature sensor and the third temperature sensor. That is, since temperatures of gases flowing through the gas hoses such as the circulation hose, the first hose, and the second hose etc. may be different from each other, temperature of gas which is injected into the peritoneal cavity may be adjusted by adjusting a flow amount of gas of each gas hose based on temperature measurement value of one or more of the second temperature sensor and the third temperature sensor.

In an embodiment, the system may be particularly a system for hyperthermic intraperitoneal chemotherapy, the drug may be an anticancer drug, and the gas may be carbon dioxide.

As described above, when the hyperthermic intraperitoneal chemotherapy is carried out by using the system of the present invention, the temperature and pressure of gas in the peritoneal cavity can be effectively maintained, the drug can be evenly sprayed into the peritoneal cavity, and thereby a chemotherapy effect can be maximized.

Hereinafter, examples of the system according to the exemplary embodiments of the present invention will be described in more detail with reference to the accompanying drawings. The present invention will be described below with reference to an example illustrated in the drawing; however, the example is described as one example, and thus it is to be construed that the technical spirit and the gist configuration and function are not limited thereto.

The description of a repeated configuration and operation will be omitted in each of the following examples. For example, a nozzle in FIG. 2 may be commonly used in all of the examples.

First Example

FIG. 1 is a schematic diagram illustrating a configuration of a system 1 including a gas circulation device and a temperature control device for temperature maintenance in a peritoneal cavity (hereinafter, referred to as 'system 1') according to an example of the present invention.

Figure 2:
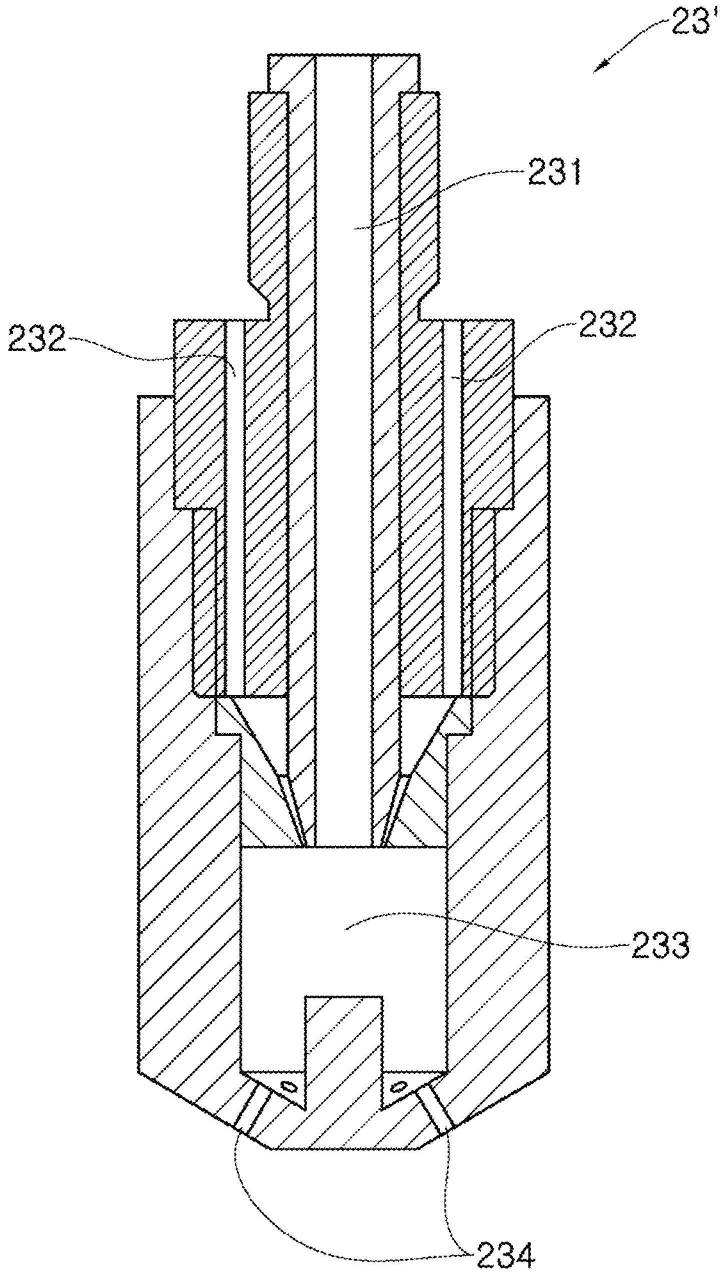
FIG. 2 is an enlarged partial cross-sectional view of part A in the system illustrated in FIG. 1.

FIG. 2 is an enlarged partial cross-sectional view of part A in the system illustrated in FIG. 1.

Figure 3:
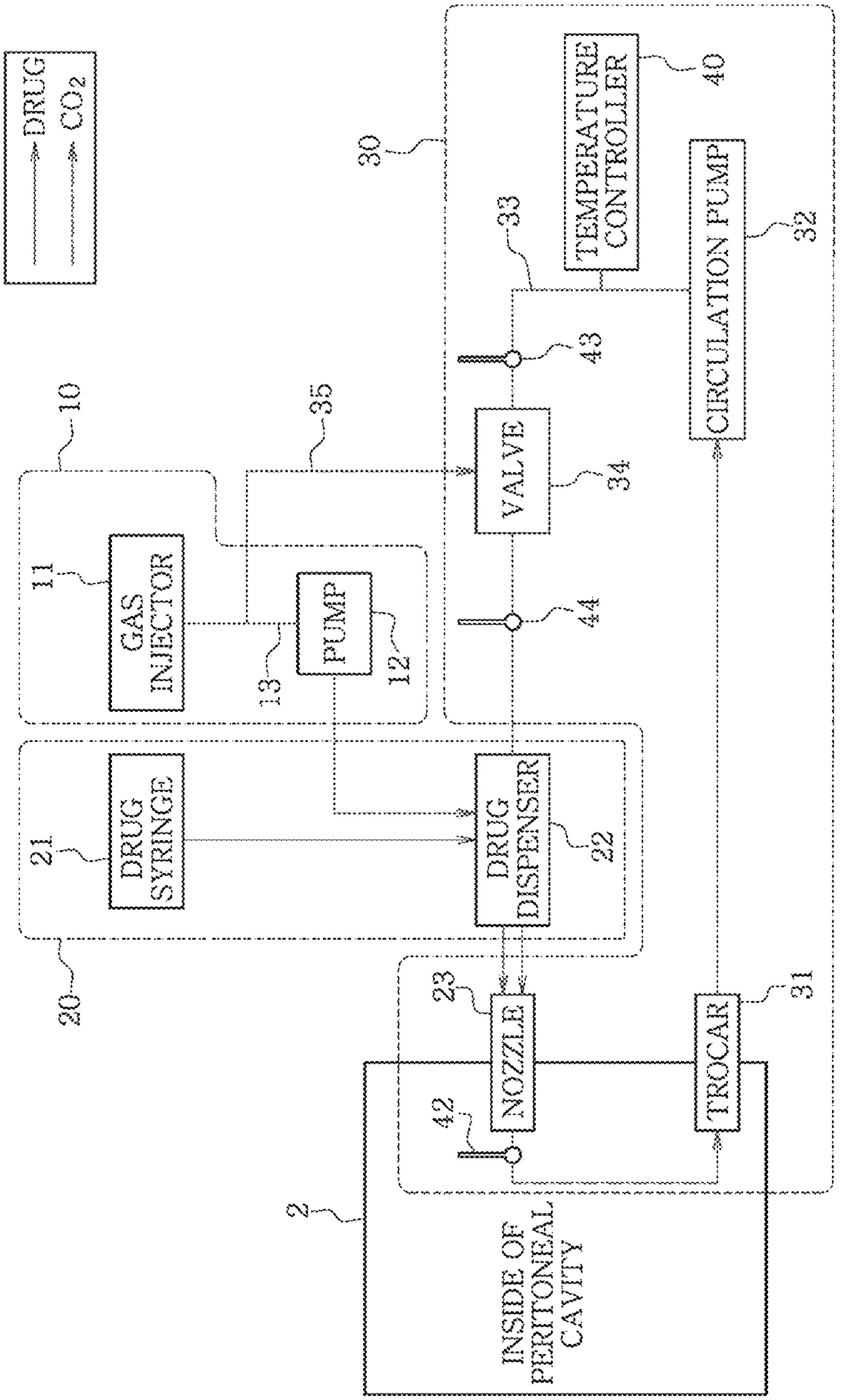
FIG. 3 is a schematic diagram illustrating the system apparatus illustrated in FIG. 1 together with flow of a drug and gas.

FIG. 3 is a schematic diagram illustrating the system apparatus illustrated in FIG. 1 together with flow of a drug and gas.

With reference to FIGS. 1 to 3, the system 1 (apparatus) includes a gas circulation device that injects, in a peritoneal cavity, pressurized gas for dilating a space of the inside 2 of a peritoneal cavity of a subject, discharges the gas outside the peritoneal cavity, and then heats and pressurizes the gas to inject the gas back into the peritoneal cavity, and a temperature control device that controls temperature of the gas circulation device. Hence, a set temperature and pressure is maintained in the space of the inside 2 of the dilated peritoneal cavity.

The gas circulation device may include a drug-and-gas spray device 20 which, as an intraperitoneal gas injecting unit that injects pressurized gas into the peritoneal cavity, performs fine spray of gas and a drug in the inside 2 of the peritoneal cavity, and the gas circulation device may include a gas supply unit 10 that supplies pressurized gas to the drug-and-gas spray device 20. In addition, the gas circulation device may include a circulation unit 30 that circulates gas.

In advance, the gas supply unit 10 may include a gas injector 11 which generates gas for dilating the inside 2 of the peritoneal cavity of the subject, a pump 12 for supplying the generated gas to the drug spray device 20, and a first hose 13 which is connected from the gas injector 11 to the drug spray device 20 and through which gas is transported.

In the gas injector 11, gas is supplied at a pressure of 12 to 14 bar, for example, and the pump 12 supplies gas at a pressure of about 3 bar to the drug-and-gas spray device 20, for example. In this case, the gas may be carbon dioxide, for example.

The drug-and-gas spray device 20 is a device that nebulizes a drug injected at a high pressure, together with gas, and evenly sprays the drug and gas in the inside 2 of the peritoneal cavity, and the drug-and-gas spray device includes a drug (for example, anticancer drug) syringe 21, a drug-and-gas dispenser 22 connected to the drug syringe, and a nozzle 23 at an end of the drug-and-gas dispenser.

The drug syringe 21 supplies the drug to be dispensed in the inside 2 of the peritoneal cavity, to the drug-and-gas dispenser 22 at a high pressure. In this case, the drug of the drug syringe 21 may be supplied to the drug-and-gas dispenser 22 at a pressure of about 1,500 kPa.

The drug-and-gas dispenser 22 is supplied with pressurized gas from the gas supply unit 10 and a drug from the drug syringe 21 and ejects the gas and the drug in the inside 2 of the peritoneal cavity of the subject. In this case, the nozzle 23 is provided at the end of the drug-and-gas dispenser 22 so as to nebulize and spray the drug.

Herein, preferably, as illustrated in FIG. 2, the nozzle 23 may be a two-fluid nozzle 23'. FIG. 2 illustrates a cross-sectional view of the two-fluid nozzle 23', and gas and a drug are together sprayed through the two-fluid nozzle 23'. Specifically, a drug supplied through a drug line 231 and gas supplied through a gas line 232 are mixed in a mixing chamber 233 and are finely sprayed through an outlet 234.

As described above, since the system 1 according to an exemplary example of the present invention nebulizes a drug by a principle of the two-fluid nozzle, a nebulization degree is excellent, a nebulization level is excellent, and a spray direction is easy to adjust as compared to a single-fluid nozzle used in the conventional PIPAC. As described above, the nebulized anticancer drug may be evenly dispersed in the inside 2 of the dilated peritoneal cavity so as to effectively work on a peritoneum to which the cancer cells metastasize.

In addition, a first temperature sensor 42 that measures temperature of gas sprayed in the inside 2 of the peritoneal cavity may be disposed at a nozzle end of the drug-and-gas spray device 20. As described below, the temperature of gas is measured by the first temperature sensor 42, and thereby the temperature of gas ejected into the peritoneal cavity of the subject may be maintained in a range of 38° C. to 42° C., preferably 41° C. to 42° C., and more preferably at 42° C. Hence, permeation of an anticancer drug into peritoneal carcinomatosis in the peritoneal cavity of a patient may be increased to maximize a chemotherapy effect.

Meanwhile, gas insufflated in the inside 2 of the peritoneal cavity of the subject pressurizes an inner wall of the peritoneal cavity of the subject to dilate the peritoneal cavity and is discharged and circulated.

For this, the circulation unit 30 discharges the gas outside the peritoneal cavity and collects the gas to the system 1, circulates the gas outside the peritoneal cavity, and injects the gas back into the peritoneal cavity.

Specifically, the circulation unit 30 may include a cannulation device (gas discharge trocar, hereinafter, first trocar) 31 which is cannulated in the peritoneal cavity and discharges gas, a circulation pump 32, a circulation hose 33, and a circulation valve 34. That is, the first trocar 31, as an intraperitoneal gas collecting device, is inserted into the inside 2 of the peritoneal cavity and collects gas in the inside 2 of the peritoneal cavity. The collected gas is supplied to the circulation valve 34 through the circulation hose 33. In this case, the circulation pump 32 pressurizes gas such that the collected gas can be circulated.

Meanwhile, a loss of gas circulating in the inside 2 of the peritoneal cavity may occur in a process of collecting the gas to the system 1. An amount of gas corresponding to the loss of gas may be supplied to the circulation valve 34 through a second hose 35 branched between the gas injector 11 and the pump 12.

The circulation valve 34 may re-supply or block the gas collected from the inside 2 of the peritoneal cavity and/or the gas supplied by the second hose 35 to the drug-and-gas dispenser 22 through opening and closing of the valve.

The temperature control device may include a temperature sensor that measures temperature of gas in order to control the temperature of the gas at a set temperature, a hot wire coil (heater) that heats the gas hose, and a temperature controller 40 that controls the hot wire coil based on a measured value of the temperature sensor.

The temperature control device may include hot wire coils 41 wound around the first hose 13, the second hose 35, and the circulation hose 33, respectively, a first temperature sensor 42, a second temperature sensor 43, and a third temperature sensor 44. For reference, the hot wire coils 41 wound around the first hose 13, the second hose 35, and the circulation hose 33, respectively, can be referred to as a first hot wire coil, a second hot wire coil, and a third hot wire coil, respectively.

The temperature controller 40 may control the gas temperature at a set temperature by adjusting a voltage applied to the hot wire coil 41 and a level of heat emission of the hot wire coil 41 according to the voltage, based on temperatures measured by the respective temperature sensors 42, 43, and 44. Consequently, the temperature of gas ejected into the inside 2 of the peritoneal cavity of the subject can be maintained at a set temperature.

Hereinafter, particularly with reference to FIG. 3, drug spray and temperature maintenance in the peritoneal cavity will be described.

When a drug and gas are ejected into the inside 2 of the peritoneal cavity of the subject, the circulation valve 34 may be in a closed state. Hence, gas which is supplied to the drug dispenser 22 is gas which is supplied from the gas supply unit 10, and supply of gas through the circulation valve 34 connected to the circulation hose 33 and the second hose 35 is blocked. The temperatures of a drug and gas ejected into the inside 2 of the peritoneal cavity are measured by the first temperature sensor 42. The temperature controller 40 controls the heater such that the temperature of the inside 2 of the peritoneal cavity can be maintained in a range of 38° C. to 42° C., preferably 41° C. to 42° C., and more preferably at 42° C., based on a measured value of the first temperature sensor 42.

Specifically, the temperature controller 40 may adjust the temperature of gas supplied through the gas supply unit 10 by adjusting the temperature of the hot wire coil 41 wound around the first hose 13 between the gas supply unit 10 and the drug dispenser 22.

Next, the drug in the drug syringe 21 is entirely dispensed into the inside 2 of the peritoneal cavity, and then the gas in the peritoneal cavity is circulated. In this case, gas collected in the circulation unit 30 comes into a state in which temperature is lowered due to heat transmission in the inside 2 of the peritoneal cavity. Consequently, the collected gas has an increase in temperature by the hot wire coil 41 wound around the circulation hose 33. The temperature of gas in the circulation hose 33 is measured by the second temperature sensor 43 and can be maintained at a set value.

On the other hand, a gas loss in the inside 2 of the peritoneal cavity of the subject may be supplemented through the second hose 35, and the temperature of gas in the second hose 35 may be lower than the temperature of gas in the circulation hose 33. Consequently, the temperature of gas in the circulation hose 33 can be maintained to be higher than 42° C., and a set value of the temperature of gas in the circulation hose 33 can be adjusted depending on an amount of gas supplied through the second hose 35.

The circulation valve 34 mixes gas which is collected from the inside 2 of the peritoneal cavity and is supplied by the circulation hose 33 and/or gas supplied by the second hose 35. The third temperature sensor 44 is disposed between the circulation valve 34 and the drug dispenser 22. Consequently, the third temperature sensor 44 measures temperature of a mixture of gas supplied by the circulation hose 33 and/or gas supplied by the second hose 35. The temperature controller 40 may adjust the temperature of a coil wound around the circulation hose 33 and/or the temperature of a coil wound around the second hose 35, based on a gas temperature measured by the third temperature sensor 44.

In addition, the first temperature sensor 42 measures the temperature of gas ejected into the inside 2 of the peritoneal cavity of the subject. The temperature controller 40 may adjust the temperature of the inside 2 of the peritoneal cavity to be maintained in a range of 38° C. to 42° C., preferably 41° C. to 42° C., and more preferably at 42° C., as described above, by adjusting the temperature of gas measured by the third temperature sensor 44 based on a measured value of the first temperature sensor 42.

As described above, the system 1 of the present invention includes a plurality of temperature sensors 42, 43, and 44, the hot wire coil 41, and the temperature controller 40 which controls the temperature sensors and the coil, thereby enabling the temperature of the inside 2 of the peritoneal cavity to be maintained constant at a set value.

Second Example

Figure 4:
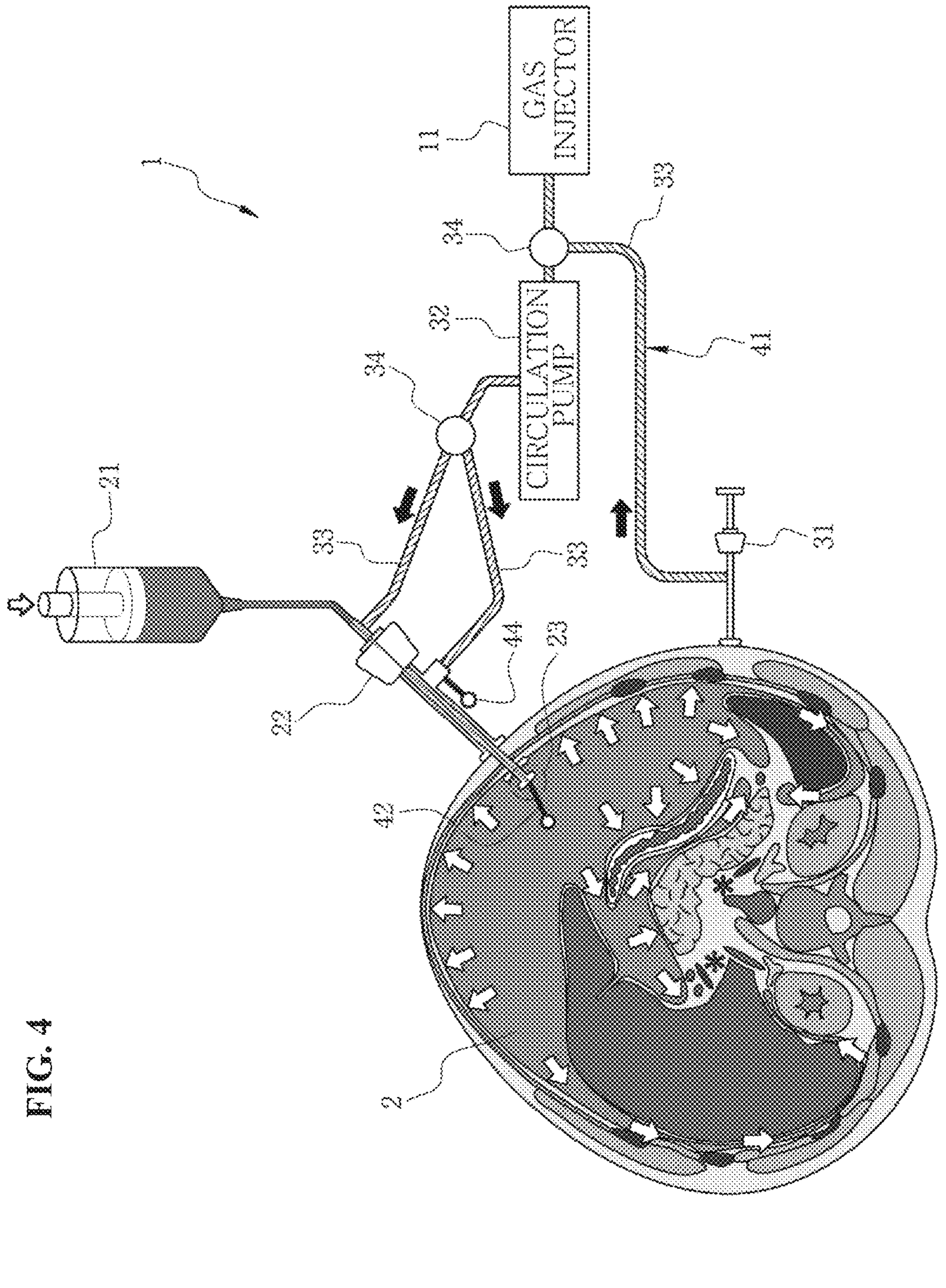
FIG. 4 is a schematic diagram illustrating a configuration of a system apparatus according to a second example of the present invention.
Figure 5:
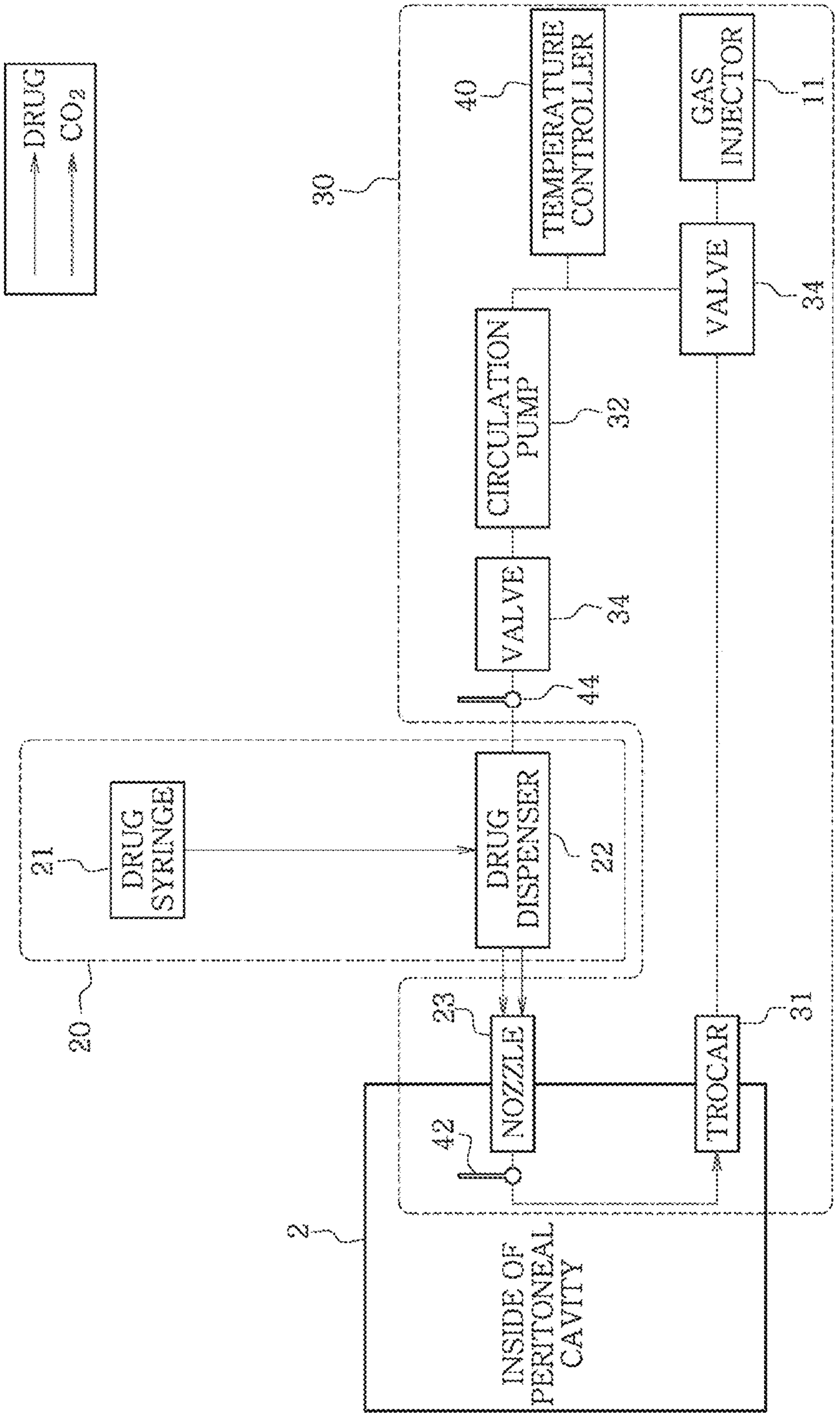
FIG. 5 is a schematic diagram illustrating the system apparatus illustrated in FIG. 4 together with flow of a drug and gas.

FIG. 4 is a schematic diagram illustrating a configuration of a system apparatus according to a second example of the present invention. FIG. 5 is a schematic diagram illustrating the system apparatus illustrated in FIG. 4 together with flow of a drug and gas.

With reference to FIGS. 4 and 5, configurations of the system 1 (apparatus) of this example is similar to those of the first example, except that the gas supply unit is directly connected to the circulation unit.

That is, the circulation unit 30 further includes the gas supply unit 10 which supplies gas to the circulation unit. Herein, the gas supply unit includes the gas injector 11 that generates gas and a gas hose (third hose) through which gas from the gas injector 11 flows and which is connected to the circulation unit 30. Similar to the first example, the gas injector 11 may supply gas at a pressure of 12 to 14 bar, for example, and the gas pressure may be adjusted through the circulation pump 32.

In addition, the circulation unit 30 may further include a three-way valve (second valve) 34 into which gas of the third hose and gas of the circulation hose flow and which discharges the gas to the circulation pump 32. In addition, the circulation unit may further include a three-way valve (third valve) 34 into which gas flows from the circulation pump 32 and which provides the gas to the drug-and-gas dispenser 22.

One or more gas hoses, for example two gas hoses, from the third valve may be connected to different locations such as a head part and a body part of the drug-and-gas dispenser 22.

Similar to the first example, the temperature sensor (third temperature sensor) 44 that measures a gas temperature of the gas hose connected to the body part may be provided, and configurations and operations other than that are the same as those of the first example.

Third Example

Figure 6:
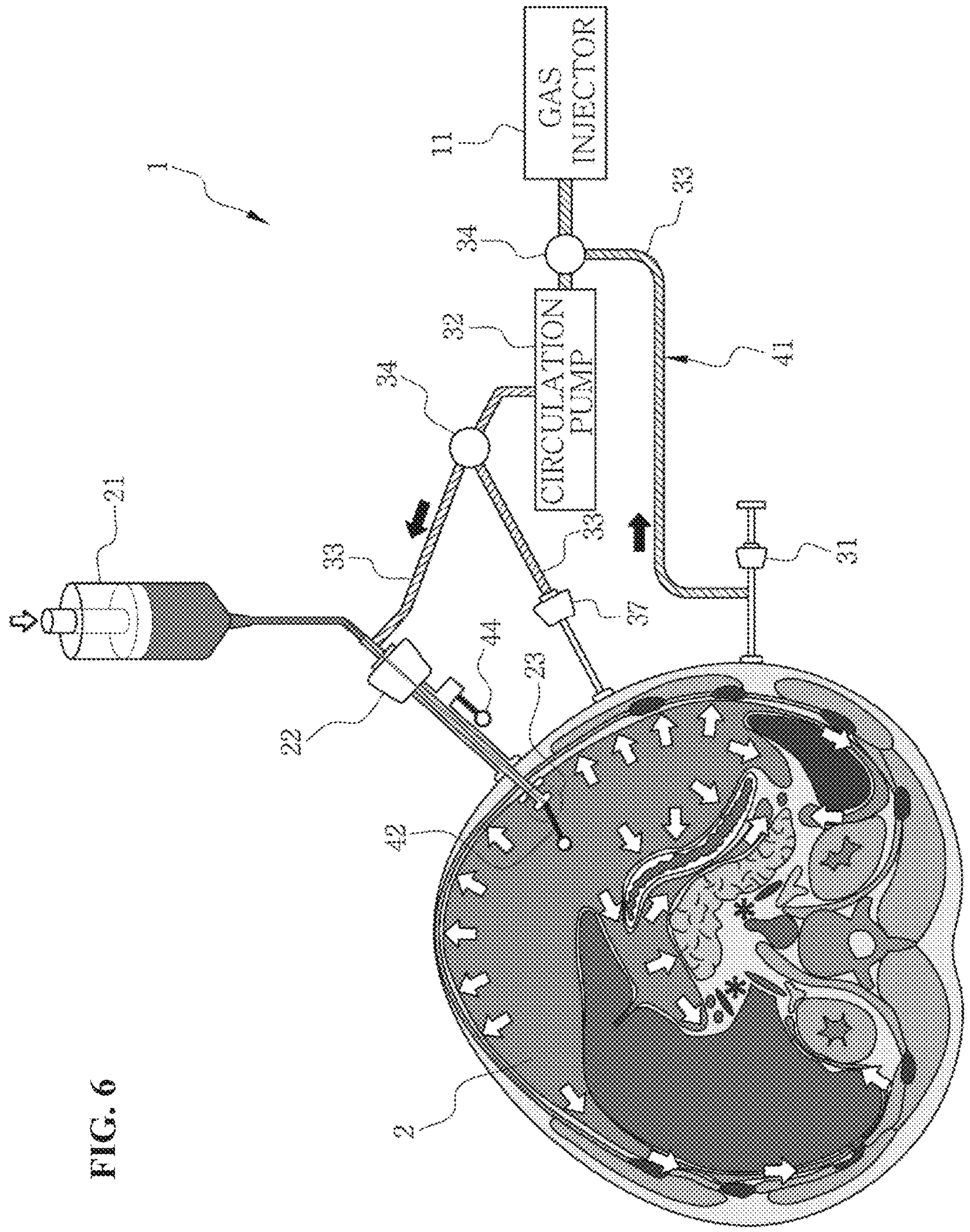
FIG. 6 is a schematic diagram illustrating a configuration of a system apparatus according to a third example of the present invention.
Figure 7:
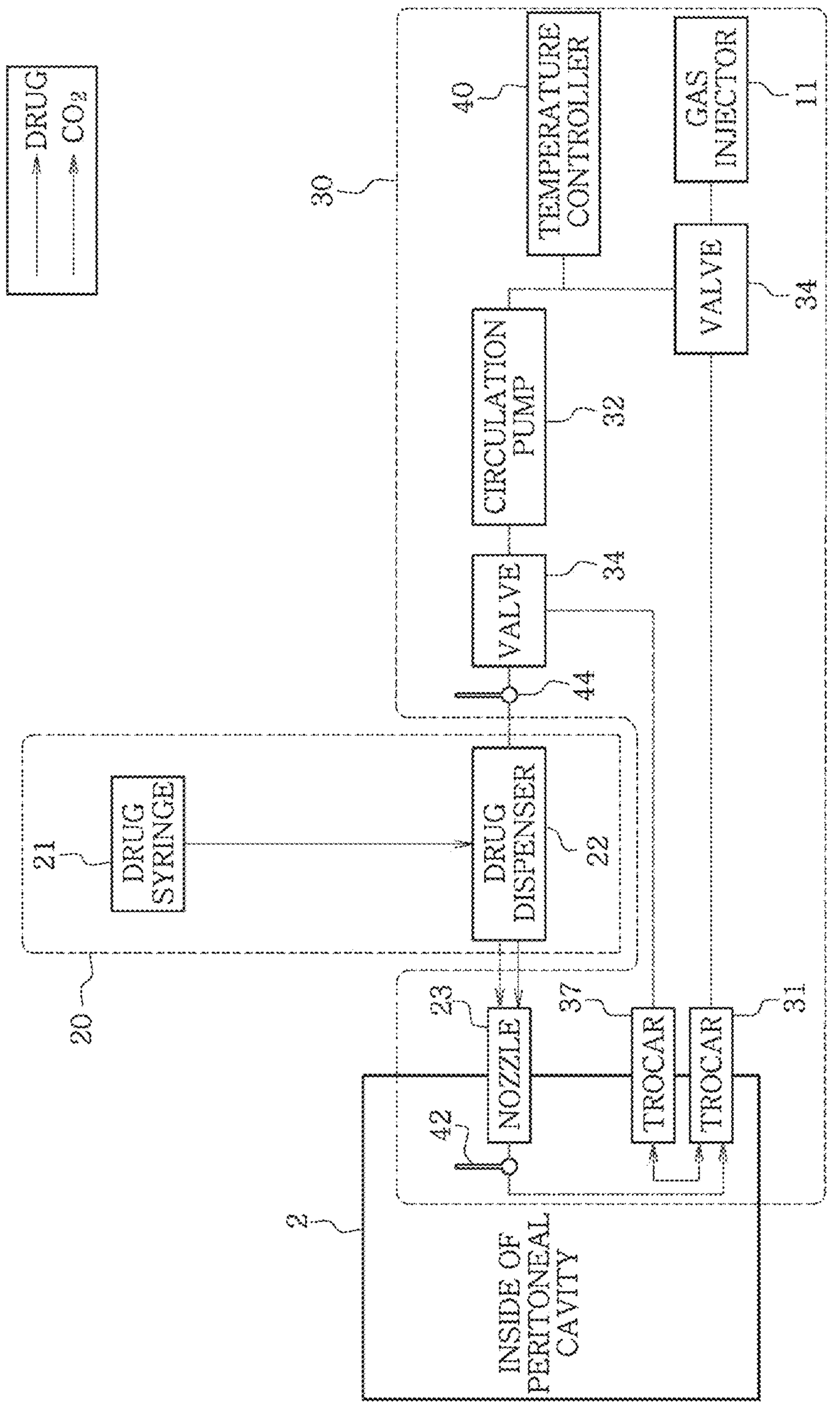
FIG. 7 is a schematic diagram illustrating the system apparatus illustrated in FIG. 6 together with flow of a drug and gas.

FIG. 6 is a schematic diagram illustrating a configuration of a system apparatus according to a third example of the present invention. FIG. 7 is a schematic diagram illustrating the system apparatus illustrated in FIG. 6 together with flow of a drug and gas.

With reference to FIGS. 6 and 7, configurations of the system 1 of this example are similar to those of the second example, except that one gas hose from the three-way valve (third valve) 34 of the circulation unit 30 is connected to the drug-and-gas dispenser 22, and the other gas hose is connected to a gas inflow trocar (hereinafter, second trocar) 37 that is a cannulation device for injecting gas, the cannulation device being cannulated into the peritoneal cavity.

Hence, a drug and gas can be together injected into the peritoneal cavity from the drug-and-gas dispenser 22, and gas can be injected into the peritoneal cavity through the separate second trocar. Configurations and operations other than that are the same as those of the second example.

Fourth Example

Figure 8:
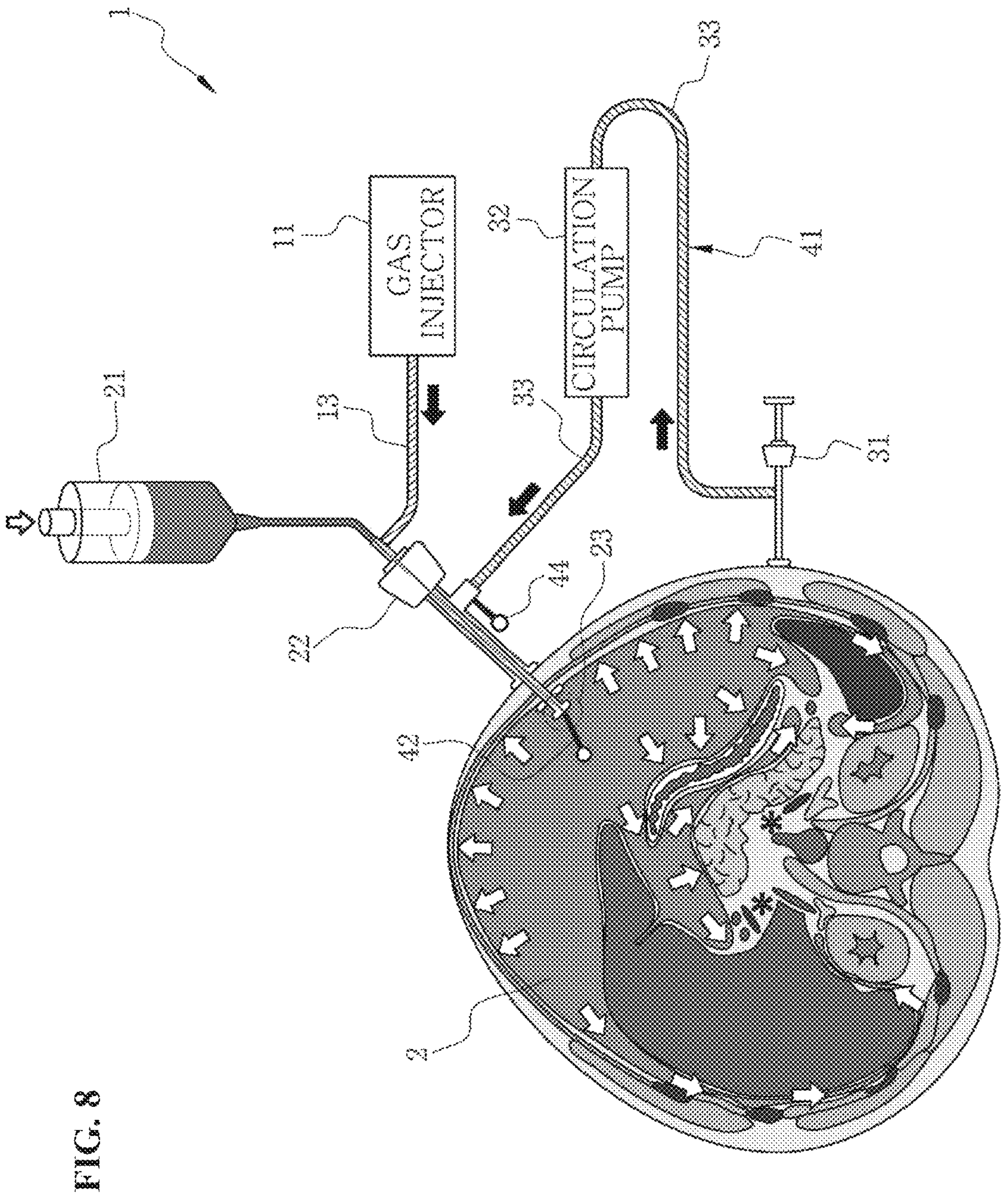
FIG. 8 is a schematic diagram illustrating a configuration of a system apparatus according to a fourth example of the present invention.
Figure 9:
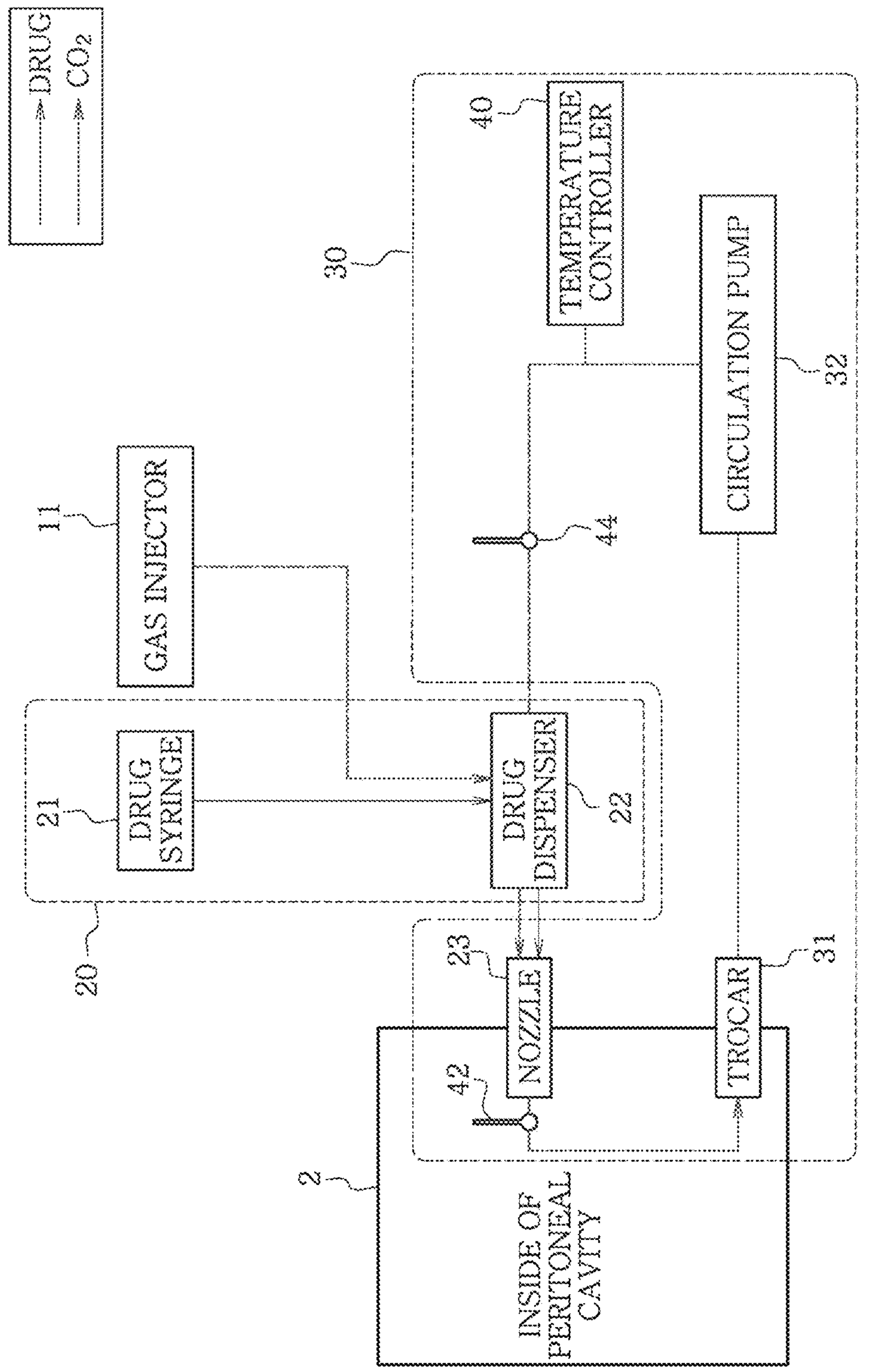
FIG. 9 is a schematic diagram illustrating the system apparatus illustrated in FIG. 8 together with flow of a drug and gas.

FIG. 8 is a schematic diagram illustrating a configuration of a system apparatus according to a fourth example of the present invention. FIG. 9 is a schematic diagram illustrating the system apparatus illustrated in FIG. 8 together with flow of a drug and gas.

With reference to FIGS. 8 and 9, configurations of the system 1 (apparatus) of this example are similar to those of the first example, except that the gas injector 11 of the gas supply unit is connected to the head of the drug-and-gas dispenser 22 without a separate branched hose or a pump.

Also, the circulation hose 33 is connected to a body part of the drug-and-gas dispenser 22 in the circulation unit 30. Here, the second temperature sensor is provided to measure temperature. Configurations and operations other than that are the same as those of the first example.

Fifth Example

Figure 10:
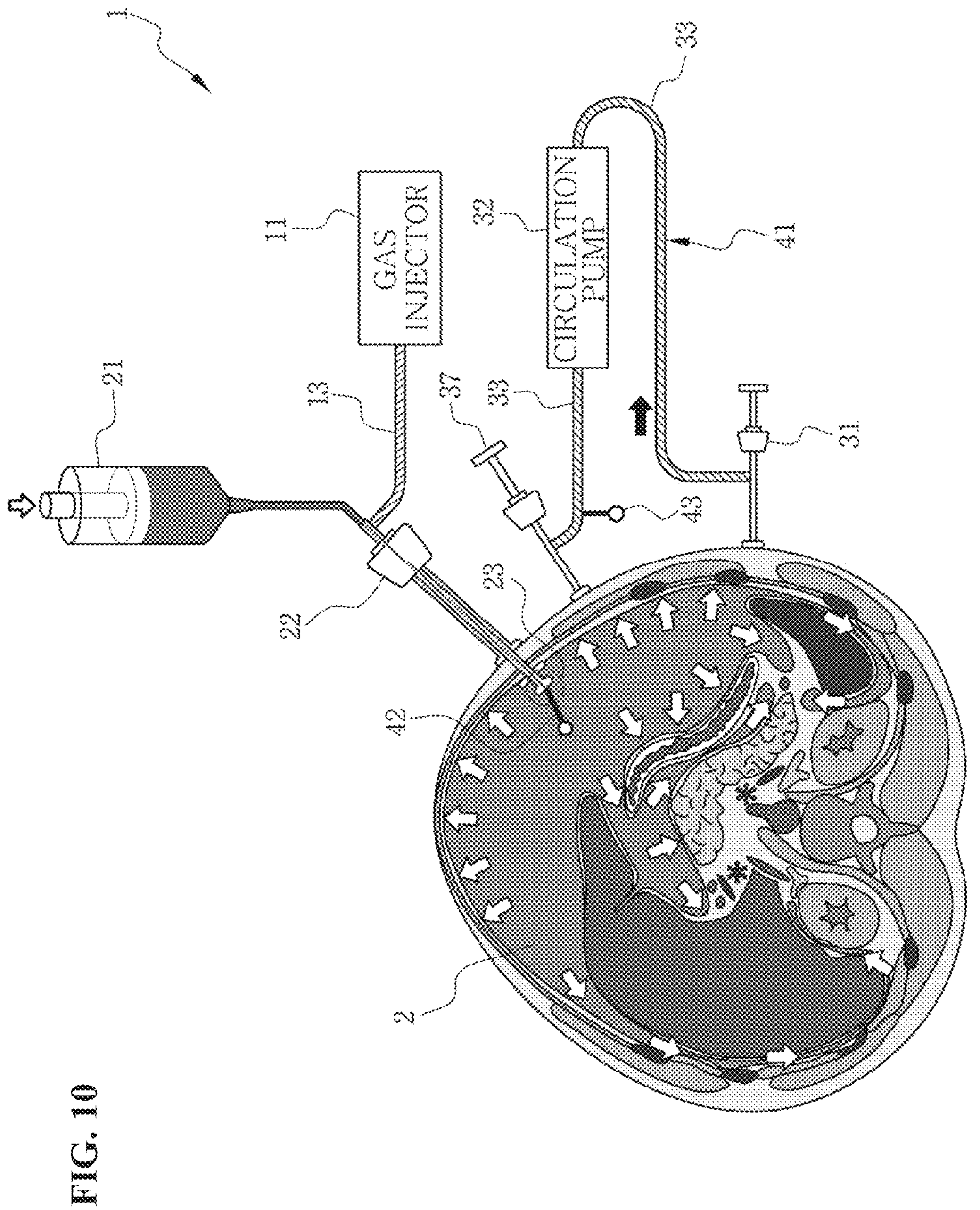
FIG. 10 is a schematic diagram illustrating a configuration of a system apparatus according to a fifth example of the present invention.
Figure 11:
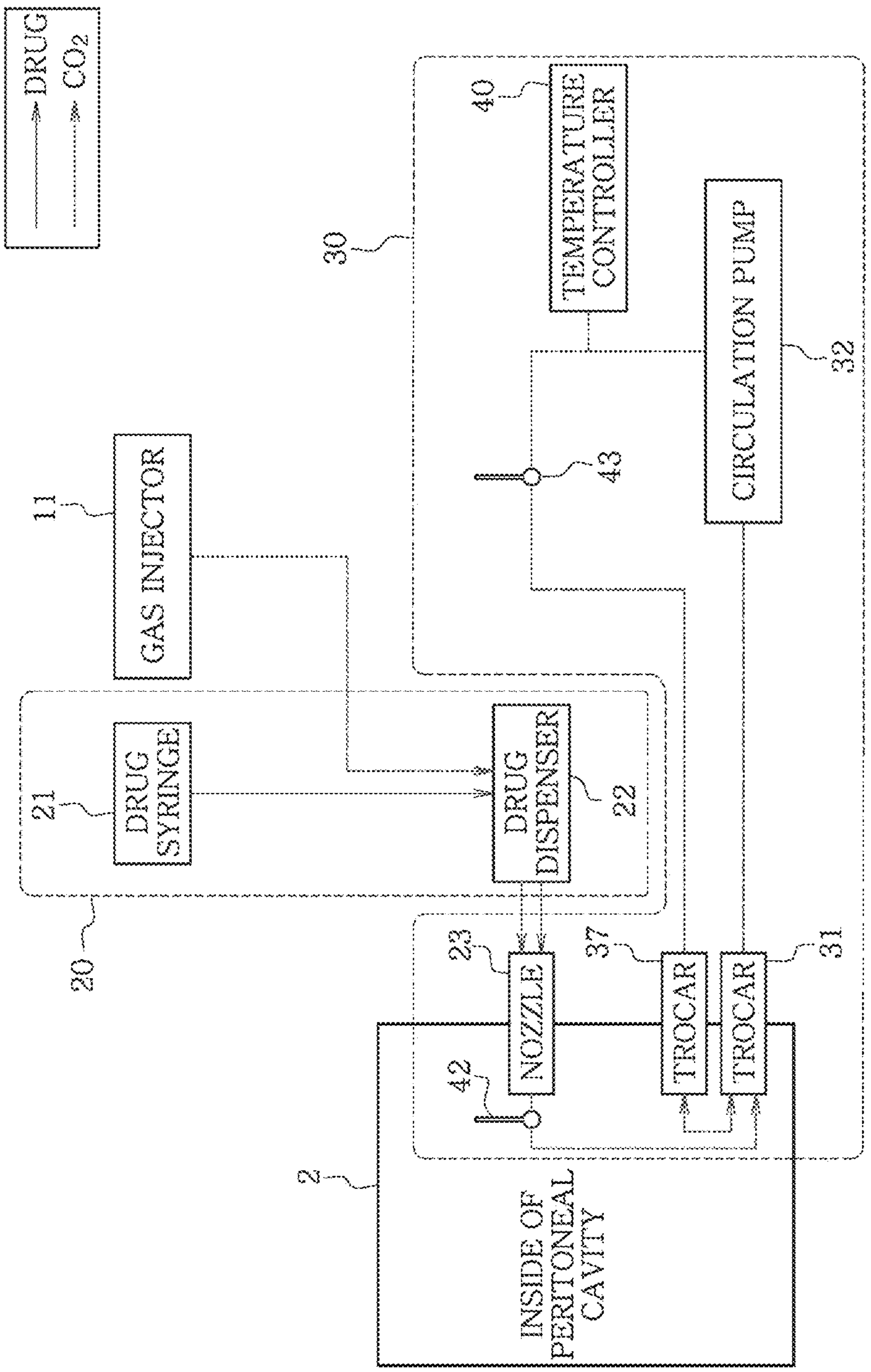
FIG. 11 is a schematic diagram illustrating the system apparatus illustrated in FIG. 10 together with flow of a drug and gas.

FIG. 10 is a schematic diagram illustrating a configuration of a system apparatus according to a fifth example of the present invention. FIG. 11 is a schematic diagram illustrating the system apparatus illustrated in FIG. 10 together with flow of a drug and gas.

With reference to FIGS. 10 and 11, configurations of the system 1 (apparatus) of this example are similar to those of the fourth example, except that the circulation hose 33 is not connected to the drug-and-gas dispenser 22 but is connected to the second trocar 37 which is a separate cannulation device for injecting gas in the circulation unit 30.

Similar to the first example, the second temperature sensor 43 for measuring a gas temperature is provided at the gas hose of the circulation unit 30. Configurations and operations other than that are the same as those of the first example.

As described above, the examples of the present invention are described in more detail with reference to the accompanying drawings; however, the present invention is not necessarily limited to the example and can be variously modified within a range without departing from the technical spirit of the present invention. Consequently, the examples disclosed in the present invention are not for limiting the technical spirit of the present invention but for describing, and the scope of the technical sprit of the present invention is not limited by the examples. Therefore, the examples described above need to be understood as exemplified examples and not as examples to limit the present invention in every aspect. The scope of the protection of the present invention should be construed by the claims below, and all technical spirits within the scope equivalent to the claims should be construed as belonging to the scope of the present invention.

INDUSTRIAL APPLICABILITY

The systems of the present invention are used as systems for hyperthermic intraperitoneal chemotherapy and can maximize an anticancer therapy effect by more effectively delivering a small amount of an anticancer drug to cancer cells while maintaining the temperature of gas in the peritoneal cavity at a set temperature.

The invention claimed is:

1. A system for circulating hyperthermic pressurized gas in a peritoneal cavity, comprising:

a gas circulation device that comprises a gas hose, which is configured to be connected to a peritoneal cavity of a subject, and a circulation pump which is connected to the gas hose and circulates gas discharged from the peritoneal cavity back to the peritoneal cavity; and a temperature control device that controls a gas temperature of the gas circulation device such that gas in the peritoneal cavity has a set temperature, wherein the gas circulation device comprises: an intraperitoneal gas injecting unit through which gas is injected into the peritoneal cavity; and a circulation unit which discharges gas from the peritoneal cavity, circulates the gas outside of the peritoneal cavity, and injects the gas back into the peritoneal cavity, and wherein the intraperitoneal gas injecting unit comprises a drug-and-gas spray device that sprays a drug together with gas during gas injection into the peritoneal cavity of the subject.

2. The system according to claim 1, wherein the temperature control device comprises: a temperature sensor which measures one or more of a gas temperature in the peritoneal cavity and a gas temperature of the gas circulation device at the outside of the peritoneal cavity; a heater that provides heat to at least a part of the gas hose of the gas circulation device; and a temperature controller that is connected to the heater and the temperature sensor, and wherein the temperature controller controls temperature of the heater such that the gas temperature in the peritoneal cavity reaches a set temperature based on a measured value of the temperature sensor.

3. The system according to claim 1, wherein the drug-and-gas spray device comprises:

a drug syringe which supplies a drug;

a drug-and-gas dispenser which is connected to the gas hose to be supplied with pressurized gas, is supplied with a drug from the drug syringe, and is cannulated into the peritoneal cavity to dispense a drug and gas into the peritoneal cavity of the subject; and a nozzle which is disposed at an end of the drug-and-gas dispenser and through which the drug and gas are sprayed into the peritoneal cavity.

4. The system according to claim 3, wherein the circulation unit comprises a first trocar which is cannulated into the peritoneal cavity and discharges gas, the gas hose which is connected to the first trocar, and the circulation pump which is connected to the gas hose and increases pressure of circulating gas, and wherein the circulating gas of the circulation unit is supplied to the drug-and-gas dispenser, or to a second trocar which is cannulated into the peritoneal cavity, or to both the drug-and-gas dispenser and the second trocar.

5. The system according to claim 4, wherein the intraperitoneal gas injecting unit further comprises a gas supply unit that supplies gas to the drug-and-gas spray device, and wherein the gas supply unit comprises:

a gas injector which generates gas; and a first hose through which gas from the gas injector flows and which is connected to the drug-and-gas spray device.

6. The system according to claim 5, wherein the circulation pump increases pressure of gas which flows through the first hose.

7. The system according to claim 5, wherein the gas supply unit further comprises a second hose which is branched from the first hose, and wherein the circulation unit further comprises a first valve into which gas of the circulation hose and the second hose flows and which discharges the gas to the drug-and-gas dispenser.

8. The system according to claim 4, wherein the circulation unit further comprises a gas supply unit that supplies gas to the circulation unit, and wherein the gas supply unit comprises:

a gas injector which generates gas; and a third hose through which gas from the gas injector flows and which is connected to the circulation unit.

9. The system according to claim 8, wherein the circulation unit further comprises a second valve into which gas of the third hose and gas of the circulation hose flows and which discharges the gas to the circulation pump.

10. The system according to claim 8, wherein the circulation unit further comprises a third valve into which gas of the circulation pump flows and which provides the gas to the drug-and-gas dispenser, and wherein one or more gas hoses from the third valve are connected to the drug-and-gas dispenser.

11. The system according to claim 10, wherein two gas hoses from the third valve are connected to different locations of the drug-and-gas dispenser, or one gas hose from the third valve is connected to the drug-and-gas dispenser and the other gas hose is connected to the second trocar.

12. The system according to claim 4, wherein the heater is a hot wire coil wound around at least a part of the gas hose, and the temperature control device comprises a first temperature sensor which measures temperature of gas sprayed into the peritoneal cavity, and wherein temperature of the hot wire coil is controlled to maintain the temperature of the gas in the peritoneal cavity in a range of temperature of 38° C. to 42° C. based on a measured value of the first temperature sensor.

13. The system according to claim 12, wherein the temperature control device further comprises one or more of:

a second temperature sensor which measures temperature of gas in the circulation unit; and a third temperature sensor which measures temperature of gas that is supplied from the circulation unit to the drug-and-gas dispenser.

14. The system according to claim 13, wherein gas supply from each gas hose is adjusted based on measured values of one or more of the second temperature sensor and the third temperature sensor.

15. The system according to claim 3, wherein the system is a system for hyperthermic intraperitoneal chemotherapy, and the drug is an anticancer drug.

16. The system according to claim 3, wherein the nozzle is a two-fluid nozzle through which the drug and gas are together sprayed into the peritoneal cavity.

17. The system according to claim 16, wherein the two-fluid nozzle comprises:

a drug line that is a passage through which a drug is supplied and that is disposed at a center of the nozzle;

two gas lines that are passages through which gas is supplied and that are separately formed at both sides of the drug line; and a mixing chamber which is connected to both the drug line and the gas line and in which a drug and gas are mixed, and wherein the mixing chamber has a discharge hole through which a mixture of a drug and gas is sprayed into the peritoneal cavity.

18. The system according to claim 1, wherein the gas is carbon dioxide.

* * * * *